(12) United States Patent
Abel et al.

(10) Patent No.: US 8,864,645 B2
(45) Date of Patent: Oct. 21, 2014

(54) HEARING IMPLANT

(75) Inventors: Eric William Abel, Dundee (GB); Zhigang Wang, Dundee (GB)

(73) Assignee: Sentient Medical Limited, Dundee (GB)

( * ) Notice: Subject to any disclaimer, the term of this patent is extended or adjusted under 35 U.S.C. 154(b) by 1602 days.

(21) Appl. No.: 11/795,137

(22) PCT Filed: Jan. 13, 2006

(86) PCT No.: PCT/GB2006/000119
§ 371 (c)(1),
(2), (4) Date: Nov. 29, 2013

(87) PCT Pub. No.: WO2006/075169
PCT Pub. Date: Jul. 20, 2006

(65) Prior Publication Data
US 2009/0043149 A1 Feb. 12, 2009

(30) Foreign Application Priority Data
Jan. 13, 2005 (GB) .................................. 0500616.8

(51) Int. Cl.
*H04R 25/02* (2006.01)
(52) U.S. Cl.
USPC ........................................................ 600/25
(58) Field of Classification Search
USPC ...................... 600/25; 310/330; 381/23.1, 60, 381/312–331
See application file for complete search history.

(56) References Cited

U.S. PATENT DOCUMENTS

| 2,397,569 | A | | 2/1946 | Strommen |
| 3,277,433 | A | | 10/1966 | Toulis |
| 3,594,514 | A | * | 7/1971 | Wingrove ........................ 600/25 |
| 3,764,748 | A | | 10/1973 | Branch et al. |
| 4,118,599 | A | | 10/1978 | Iwahara et al. |
| 4,139,728 | A | | 2/1979 | Haramoto et al. |
| 4,219,696 | A | | 8/1980 | Kogure et al. |

(Continued)

FOREIGN PATENT DOCUMENTS

| CN | 1922402 A | 2/2007 |
| CN | 1937970 A | 3/2007 |

(Continued)

OTHER PUBLICATIONS

Japanese Office Action "Notice of Reason for Rejection" with mailing date of Feb. 1, 2011; Japanese Patent Application No. 2007-550843 with translation.

(Continued)

*Primary Examiner* — Charles A Marmor, II
*Assistant Examiner* — Catherine E Burk
(74) *Attorney, Agent, or Firm* — Studebaker & Brackett PC

(57) ABSTRACT

The present invention concerns an actuator for an implantable hearing aid for implantation into the human middle ear. The actuator comprises a substantially elongate piezoelectric component (34, 36) having first and second operating end faces (41, 43), said end faces extending substantially at right angles to the longitudinal axis of the piezoelectric component. Also there is provided a frame component comprising at least one flextensional amplifier element (32), the flextensional amplifier element being integral with and connecting first and second frame end portions (42, 44), the first and second frame end portions also extending substantially at right angles to longitudinal axis of the piezoelectric component when fitted thereto, whereby the first and second end portions are in contact with the piezoelectric component end faces.

34 Claims, 8 Drawing Sheets

(56) References Cited

U.S. PATENT DOCUMENTS

| | | | |
|---|---|---|---|
| 4,624,672 A | 11/1986 | Lenkauskas | |
| 4,729,366 A * | 3/1988 | Schaefer | 600/25 |
| 4,759,070 A | 7/1988 | Voroba et al. | |
| 4,774,515 A | 9/1988 | Gehring | |
| 4,809,708 A | 3/1989 | Geisler et al. | |
| 4,845,688 A * | 7/1989 | Butler | 367/174 |
| 4,901,353 A | 2/1990 | Widin | |
| 4,957,478 A * | 9/1990 | Maniglia | 600/25 |
| 5,015,225 A | 5/1991 | Hough et al. | |
| 5,173,944 A | 12/1992 | Begault | |
| 5,233,665 A | 8/1993 | Vaughn et al. | |
| 5,279,292 A | 1/1994 | Baumann et al. | |
| 5,303,306 A | 4/1994 | Brillhart et al. | |
| 5,325,436 A | 6/1994 | Soli et al. | |
| 5,434,924 A | 7/1995 | Jampolsky | |
| 5,436,975 A | 7/1995 | Lowe et al. | |
| 5,456,654 A * | 10/1995 | Ball | 600/25 |
| 5,707,338 A | 1/1998 | Adams et al. | |
| 5,729,077 A | 3/1998 | Newnham et al. | |
| 5,825,894 A | 10/1998 | Shennib | |
| 5,879,283 A | 3/1999 | Adams et al. | |
| 5,913,815 A | 6/1999 | Ball et al. | |
| 5,984,859 A | 11/1999 | Lesinski | |
| 6,001,129 A | 12/1999 | Bushek et al. | |
| 6,137,889 A | 10/2000 | Shennib et al. | |
| 6,261,224 B1 | 7/2001 | Adams et al. | |
| 6,315,710 B1 | 11/2001 | Bushek et al. | |
| 6,325,755 B1 | 12/2001 | Bushek et al. | |
| 6,364,825 B1 * | 4/2002 | Kennedy et al. | 600/25 |
| 6,398,717 B1 * | 6/2002 | Leysieffer et al. | 600/25 |
| 6,482,144 B1 | 11/2002 | Muller | |
| 6,490,881 B1 | 12/2002 | Sinclair et al. | |
| 6,537,199 B1 | 3/2003 | Müller et al. | |
| 6,537,200 B2 | 3/2003 | Leysieffer et al. | |
| 6,554,761 B1 | 4/2003 | Puria et al. | |
| 6,629,922 B1 * | 10/2003 | Puria et al. | 600/25 |
| 6,671,559 B2 * | 12/2003 | Goldsmith et al. | 607/57 |
| 6,717,333 B2 * | 4/2004 | Hermle et al. | 310/328 |
| 6,875,166 B2 | 4/2005 | Kroll et al. | |
| 7,289,639 B2 | 10/2007 | Abel et al. | |
| 2003/0097178 A1 | 5/2003 | Roberson et al. | |
| 2005/0165481 A1 | 7/2005 | Steinhardt et al. | |
| 2006/0189841 A1 * | 8/2006 | Pluvinage | 600/25 |
| 2007/0021833 A1 | 1/2007 | Awengen et al. | |
| 2008/0065002 A1 | 3/2008 | Lobl et al. | |
| 2008/0107546 A1 | 5/2008 | Falch et al. | |
| 2008/0208337 A1 | 8/2008 | Awengen et al. | |
| 2009/0023976 A1 | 1/2009 | Cho et al. | |
| 2009/0131742 A1 | 5/2009 | Cho et al. | |

FOREIGN PATENT DOCUMENTS

| | | |
|---|---|---|
| DE | 28 44 979 A1 | 4/1980 |
| DE | 35 08 830 A1 | 9/1986 |
| DE | 29701534 U1 | 3/1997 |
| DE | 202007017910 U1 | 3/2008 |
| EP | 1498088 A2 | 1/2005 |
| JP | 60-154800 | 8/1985 |
| JP | S61-42284 A | 2/1986 |
| JP | H06-310771 A | 11/1994 |
| RU | 2 096 027 C1 | 11/1997 |
| WO | 92/18066 A1 | 10/1992 |
| WO | 97/23117 A1 | 6/1997 |
| WO | WO 97 32385 A1 | 9/1997 |
| WO | WO 00 76271 A1 | 12/2000 |
| WO | WO 03 063542 A2 | 7/2003 |

OTHER PUBLICATIONS

Yanagihara et al., "Intraoperative Assessment of Vibrator-Induced Hearing", Advanced Audiology, vol. 4, pp. 124-133, 1988.

Yanagihara et al., "Long-Term Results Using a Piezoelectric Semi-Implantable Middle Ear Hearing Device: The Rion Device E-Type", Otolaryngologic Clinics of North America, vol. 34, No. 2, pp. 389-400, Apr. 2001.

Zenner et al., "Total Implantation of the Implex TICA Hearing Amplifier Implant for High-Frequency Sensorineural Hearing Loss: The Tübingen University Experience", Otolaryngologic Clinics of North America, vol. 34, No. 2, pp. 417-446, Apr. 2001.

Maassen et al., "Total Implantation of the Active Hearing Implant TICA for Middle Ear Diesase: A Temporal Bone Study", Annals of Otolaryngology, Rhinology, and Laryngology, vol. 110, vol. 1, pp. 912-916, Oct. 2001.

Hough et al., "Semi-Implantable Electromagnetic Middle Ear Hearing Device for Moderate to Severe Sensorineural Hearing Loss", Otolaryngologic Clinics of North America, vol. 34, No. 2, pp. 401-416, Apr. 2001.

Hough et al., Middle Ear Electromagnetic Semi-Implantable Hearing Device: Results of the Phase II SOUNDTEC Direct System Clinical Trial., Otology & Neurotology, Inc., vol. 23, No. 6, pp. 895-903, Nov. 2002.

Shih et al., "Scaling Analysis for the Axial Displacement and Pressure of Flextensional Transducers", Journal of American Ceramic Society, vol. 80, No. 5, pp. 1073-1078, 1997.

Gan et al., "Mass Loading on the Ossicles and Middle Ear Function", Annals of Otolaryngology, Rhinology, and Laryngology, vol. 110, No. 5 (Pt. 1), pp. 478-485, May 2001.

Dogan et al., "Composite Piezoelectric Transducer with Truncated Conical Endcaps *Cymbal*", IEEE Transactions on Ultrasonics, Ferroelectrics, and Frequency Control, vol. 44, No. 3, pp. 597-605, May 1997.

Brigham et al., "Present Status in the Design of Flextensional Underwater Acoustic Transducers", Summary of paper in Acoustical Society of America 77$^{th}$ Meeting, vol. 46, No. 1 (Pt. 1), p. 92, 1969.

Newnham et al., "Flextensional *Moonie* Actuators", 1993 Ultrasonics Symposium, pp. 509-513, 1993.

Australian Office Action dated Sep. 1, 2010; Patent Application No. 2006205655.

The Japanese Office Action "Notice of Reason for Rejection" dated Jan. 10, 2012, which corresponds to Japanese Patent Application No. 2007-550843 and is related to U.S. Appl. No. 11/795,137 with translation.

The communication pursuant to Article 94(3) EPC dated Feb. 3, 2009, which corresponds to EP Application No. 06 700 906.8-2320 and is related to U.S. Appl. No. 11/795,137.

The Russian Office Action "Enquiry" dated Dec. 22, 2009, which corresponds to Russian Patent Application No. 2007131471/14(034299) and is related to U.S. Appl. No. 11/795,137 with translation.

The Canadian Office Action dated Oct. 1, 2012, which corresponds to Canadian Patent Application No. 2,594,761 and is related to U.S. Appl. No. 11/795,137.

The Australian Office Action dated Jan. 25, 2013, which corresponds to Australian Patent Application No. 2008249763 and is related to U.S. Appl. No. 11/795,137.

An Office Action issued by the Goverment of India Patent Office on Jun. 24, 2013, which corresponds to Indian Patent Application No. 1102/MUMNP/2007 and is related to U.S. Appl. No. 11/795,137.

The Office Action issued by the Canadian Intellectual Property Office on Oct. 1, 2012, which corresponds to Canadian Patent Application No. 2,594,761 and is related to U.S. Appl. No. 11/795,137.

International Search Report dated Mar. 20, 2006 for International Application No. PCT/GB2006/000119.

Written Opinion of the International Search Report for International Application No. PCT/GB2006/000119. Mar. 8, 2007.

European Office Action issued on Aug. 22, 2013, which corresponds to EP087096673-1662 and is related to U.S. Appl. No. 11/795,137.

Japanese Office Action issued on Jul. 16, 2013, which corresponds to JP2009-552280 and is related to U.S. Appl. No. 11/795,137; with translation.

Canadian Office Action issued on Jul. 18, 2013, which corresponds to Canadian Patent Application No. 2,724,137 and is related to U.S. Appl. No. 11/795,137.

An Office Action issued by the Canadian Intellectual Property Office on Aug. 22, 2013, which corresponds to Canadian Patent Application No. 2,594,761 and is related to U.S. Appl. No. 11/795,137.

(56) References Cited

OTHER PUBLICATIONS

An Office Action issued by the Japanese Patent Office on Sep. 25, 2013, which corresponds to Japanese Patent Application No. 2010-507007 and is related to U.S. Appl. No. 11/795,137.

Notice of Allowance issued by the Australian Patent Office on Aug. 16, 2013, which corresponds to Australian Patent Application No. 2008222478 and is related to U.S. Appl. No. 11/795,137.

The forth Notification of Office Action issued by the State Intellectual Property Office of China on Nov. 22, 2013, which corresponds to Chinese Patent Application No. 200880014635.X and is related to U.S. Appl. No. 11/795,137; with English language translation.

Leiner, et al.; "A Pathway for Information Transmission to the Inner Ear Application to Cochlear Implants"; ASAIO Journal 1992; 38: pp. M253-M256.

"First Notification of Office Action" issued by the State Intellectual Property Office of China on Jan. 28, 2014, which corresponds to Chinese Patent Application No. 201080032713.6 and is related to U.S. Appl. No. 11/795,137; with English language translation.

"First Notification of Office Action" issued by the State Intellectual Property Office of China on Feb. 27, 2014, which corresponds to Chinese Patent Application No. 201080032735.2 and is related to U.S. Appl. No. 11/795,137; with English language translation.

An Office Action issued by the Canadian Patent Office on Dec. 13, 2013, which corresponds to Canadian Patent Application No. 2,717,361 and is related to U.S. Appl. No. 11/795,137.

An Office Action; "Advisory Action Before the Filing of an Appeal Brief," issued by U.S. Patent Office on Feb. 11, 2014, which corresponds to U.S. Appl. No. 12/599,530.

* cited by examiner

HEARING IMPLANT

The present invention relates to devices for aiding the hearing impaired. More specifically the present invention relates to the provision of electromechanical actuators of which can be directly attached to the small bones of the middle ear for amplifying vibrations generated by sound signals.

Sensorineural deafness is by far the most common type of Hearing loss. Deafness affects 9 million people in the United Kingdom, of which over 80% have sensorineural deafness (source Defeating Deafness, United Kingdom). Causes include congenital, bacterial, high intensity noise and, especially, the ageing process, with a significant proportion of those affected being over 60 years old. Hearing impairment is the third most common chronic problem affecting the ageing population—and one of the least diagnosed. There is also an increased prevalence in some sections of the younger age group, due to exposure to loud noise.

There are currently no effective means of repairing the cochlea or the nervous pathways to the brain. For most patients hearing can be restored adequately by sufficient amplification of sound with a hearing aid. Conventional hearing aids have a number of problems: acoustic feedback (because the microphone is very close to the speaker), inadequate sound quality and discomfort due to occlusion of the ear canal. Many are also undesirable from the social point of view in that the appearance of wearing a hearing aid can cause users to feel that they are seen to be handicapped. The alternative is an implantable device.

Middle ear implants (MEIs) provide mechanical amplification by vibrating the ossicular chain. They are intended for patients with moderate to severe sensorineural hearing loss who still have residual hearing. They could potentially benefit up to 50% of all people with hearing loss.

Such middle ear implants can utilise actuators in the form of electromechanical displacement devices, that control the position of a component through the use of an electric field. In this regard, piezoelectric actuators are known and are based on the piezoelectric effect, whereby certain crystalline materials exhibit the property of changing shape when subjected to an externally applied voltage. In this connection, a flextensional actuator can be defined as a piezoelectric element (or a stack of piezoelectric elements) connected to a flexible mechanical structure that converts and amplifies the output displacement of the piezoelectric element or stack of piezoelectric elements. The performance of the flextensional component depends on the distribution of rigidity in the material from which the flextensional component is made, its shape and therefore also on the coupling structure topology.

Many types of piezoelectric actuator have been proposed, especially since the nineteen-fifties and, these are now described by those skilled in the art according to a series of classes defined by shape (Brigham and Royster, 1969). There were originally five classes but at least seven classes are now generally accepted. It is well known to those skilled in the art that minor changes in the design of actuators which may be generally similar in appearance can make highly significant differences to performance and even feasibility of use for a particular application.

Multilayer actuators provide high generative force and response speed but do not exhibit high displacement. Bimorph actuators can exhibit high displacement but have less generative force and slower response speed. Flextensional actuators are generally used with multilayer piezoelectric elements in order to increase displacement but at the cost of lower driving force for applications where the force generated is still sufficient. The Moonie actuator (Newnham, 1991) is one such actuator with a performance that, to some extent, bridges the gap between the multilayer actuator and bimorph. However, a reported disadvantage of the Moonie actuator is that the flexible mechanical structures which generate the flexural motion (which are called "end caps" by Newnham) and their assembly require labour intensive processes in commercial production.

In Dogon et al., *Composite Piezoelectric Transducer with Truncated Conical Endcaps "Cymbal"*, and U.S. Pat. No. 5,729,077 to Newnham et al., there are proposed developments to the Moonie device described as a "cymbal" actuator with increased displacement, larger generative forces and simpler end cap design. The cymbal actuator comprises a cylindrical ceramic element sandwiched between two truncated conical metal end caps. Dogon et al. suggest that the metal end caps of their design are more cost-effective to manufacture by stamping and that the cymbal actuator exhibits a much higher displacement than the same size of ceramic element. The displacement mechanism of this actuator is a combination of flextensional motion and rotational motion which, it is claimed, provides a more homogeneous displacement over a wider section than the basic Moonie actuator or a variant thereof having ring shaped grooved end caps.

Dogon et al describe stacking individual actuators together in order to reach higher displacements and they also contemplate miniaturised designs, however, this is in the context of underwater sensing devices down to a few centimetres in size rather than devices which might be made small enough to implant in the middle ear.

Middle ear implants with actuators based on the use of piezoelectric or electromagnetic transducers have been proposed. Actuators utilising piezoelectric transducers have the potential benefit of providing mechanical movement directly from an electrical signal to vibrate the ossicular chain as desired.

Actuators comprising piezoelectric transducers made from lead zirconate titanate (PZT) have been used in different configurations to provide assistance to the hearing impaired. A partially implantable piezoelectric middle ear implant (P-MEI™) based on a piezoelectric bimorph vibrator (FIG. 1) was developed in Japan, Yanagihara et al., *Intraoperative Assessment of Vibrator-Induced Hearing*; and Yanagihara et al., *Long-Term Results Using a Piezoelectric Semi-Implantable Middle Ear Hearing Device: The Rion Device E-Type*. The bimorph vibrator 1 has a similar structure to that of a bimetallic strip. It has two strips of piezoelectric film 2,4 of opposite polarities, adhered together to form a bending, or bimorph vibrator. An applied voltage indicated at 6 causes one of the strips to lengthen while the other contracts, causing the unit to bend. The vibrator is 1.4 mm wide, 0.6 mm thick, and 7 mm long, and is anchored with a bracket at an appropriate site in the middle ear.

Manufactured by Rion Co. Ltd. (Japan), the partially implantable middle ear implant (P-MEI™) was approved in 1993 in Japan for extended clinical trials and has been tested in human subjects The P-MEI™ (see FIG. 2) consists of an external unit 8 and an internal unit 10. The external unit 8 consists of a microphone, amplifier and primary induction coil. This unit, powered by a battery, transmits the amplified electrical signal by electromagnetic induction to an internal secondary induction coil 12, the output of which is connected electrically to the piezoelectric ceramic bimorph vibrator 1 in direct contact with the stapes head 13, via a hydroxyapatite tube 14. This arrangement requires the other bones of the ossicular chain to be removed which limits its application to a small group of patients with a severely damaged middle ear that could not be rehabilitated by ordinary middle ear surgery. The maximal output power of the vibrator element for clinical use compensates only for a 50 dB loss of bone conduction at 1 kHz. The P-MEI™ device is, therefore, only indicated for use in patients with conductive and mixed hearing losses.

The Implex™ middle ear implant system TICA™ (Total Implantable Communication Assistance) was developed in Germany, Zenner et al., *Total Implantation of the Implex TICA Hearing Amplifier Implant for High-Frequency Sensorineural Hearing Loss: The Tubingen University Experience*. This MEI is based on a piezoelectric disc bender 16, as shown in FIG. 3*a*. There are two modes of vibration for a ceramic disc bender, viz. I its radial and thickness directions, governed by its material piezoelectric coefficients d31 and d33, respectively. Because the circumference of the ceramic element 18 is constrained by a supporting metal element 20 (usually a brass plate), there is no effective radial displacement and the energy generated for movement in this direction is redirected to amplify the displacement of the ceramic disc bender 16 in its thickness direction. Larger versions of this design are used in great quantities in such items as the buzzers of telephones and alarm clocks. In addition, the TICA™ device has a hermetically sealed and biocompatible housing 22 (FIG. 3*b*), inside which is located the piezoelectric ceramic disc bender. Vibrations are transmitted to the ossicular chain by a mechanically rigid titanium element 24 attached in the central area of the housing. The actuator had a diameter of 9.3 mm and there was a smaller version of 8.5 mm diameter, Maassen et al., *Total Implantation of the Active Hearing Implant TICA for Middle Ear Disease: a Temporal Bone Study*, both with a 3 mm thick titanium disc housing, the assembled devices having a total mass of 0.4 g.

A titanium coupling probe 28, 0.5 mm in diameter, is mounted in the centre of the exterior of the titanium disc. At an applied voltage of 1 V (rms) the unloaded actuator displacement was about 60 nm from 250 Hz up to about 6 kHz. The supporting structure for both of these prior art devices are fixed to the skull which requires complex surgery. Both devices also present the potential problem of feedback resulting from vibration of the skull, as well as from the intended vibratory stimulation of the ossicular chain. The TICA™ device was recently withdrawn.

Another type of electronic implantable middle ear hearing aid is based on electromagnetic principles. An electromagnetic actuator consists of a coil in which an electric current induces a magnetic flux to drive an adjacent magnet. In this "moving magnet" system, the magnet is attached to the vibratory structures of the middle ear and the coil is positioned nearby, either in the external ear canal or, with a separate fixation, in the middle ear. Magnets can be placed on the tympanic membrane or on the incus or on the stapes. Such a magnetic system is described, for example, in U.S. Pat. No. 5,015,225, to Hough et al, where the electromagnetic signal, derived from the sound detected by a microphone, is generated by a transmitter placed either in the outer ear canal or in the mastoid area of the temporal bone. Magnets, located on the ossicular chain or substituting for part of the ossicular chain, vibrate in sympathy with the output from the transmitter. A recent development of devices with implanted magnets on the stapes has been to improve coaxial electromagnetic alignment of the external ear canal. The distance between the coil and the magnet has also been reduced to less than 4 mm, Hough et al., *Semi-Implantable Electromagnetic Middle Ear Hearing Device for Moderate to Severe Sensorineural Hearing Loss*. This middle ear implant, named the SOUNDTEC™ Direct Drive™ hearing system (SoundTec™, Oklahoma City, Okla., USA), has undergone phase II clinical trials, Hough et al., *Middle Ear Electromagnetic Semi-Implantable Hearing Device: Results of the Phase II SOUNDTEC Direct System Clinical Trial*. The use of such magnetic devices has the advantage that only the magnetic actuator has to be fitted in the middle ear but the electromagnetic transmitter must be positioned sufficiently close to the magnet to provide vibrations of sufficient magnitude to properly stimulate the auditory system in order to improve hearing adequately.

In U.S. Pat. No. 6,629,922 to Puria et al the authors describe a flextensional actuator for surgically implantable hearing aids wherein a piezo element is disposed between two end caps which function as flextensional amplifiers and these three components are glued together with suitable adhesive means. The authors refer to the actuator as a prismatoid type, however, it conforms with the widely accepted description of a cymbal actuator; a point which is conceded in several parts of the description, for example, with respect to their FIG. 4F. The authors contemplate encasing the actuator in biocompatible material to isolate it from the body.

An object of the present invention is to seek to provide a hearing aid actuator which alleviates the problems associated with the known arrangements discussed above.

It is a further object of the present invention to seek to provide an actuator for attachment to the ossicular bones of the human middle ear to generate amplified mechanical vibrations of the ossicular bones, without the requirement for removing any part of said ossicular bones, said actuator for amplifying sound vibration for the improvement of hearing for persons with hearing loss.

It is a yet further object of the present invention to provide hearing aid systems incorporating an actuator of the present invention.

According to an aspect of the present invention there is provided an actuator for a hearing aid for implantation into the human middle ear, the actuator comprising: a substantially elongate piezoelectric component having first and second operating end faces, said end faces extending substantially at right angles to the longitudinal axis of the piezoelectric, component; and a frame component comprising at least one flextensional amplifier element, the flextensional amplifier element being integral with and connecting first and second frame end portions, the first and second frame end portions also extending substantially at right angles to longitudinal axis of the piezoelectric component when fitted thereto, whereby the first and second end portions are in contact with the piezoelectric component first and second operating end faces.

According to yet a further aspect of the present invention there is provided an actuator for a hearing aid for implantation into the human middle ear for amplifying sound vibration comprising: a piezoelectric component comprising a piezoelectric element or stack of said elements or an array of said stacks of said elements, the or each piezoelectric component having first and second operating ends; and a frame component comprising at least one flextensional amplifier element, said frame component further having first and second end portions integral with and disposed substantially at right angles to the main axis of said flextensional amplifier element or amplifier elements, such that said first and second end portions of said frame component provide close receival and fitting means for said first and second operating ends of said piezoelectric component, said flextensional amplifier element or amplifier elements operating with displacement substantially orthogonal with respect to the operating direction of said piezoelectric component; and the assembly created thereby constituting an actuator surgically implantable into the middle ear through the ear canal and via the incised and folded back tympanum; whereby said actuator may be secured with securing means to one or more bones of the human ossicular chain without the removal or destruction of any part of any said bone.

The present invention provides an actuator for attachment to the ossicular chain of the middle ear, said actuator being adapted for contact with both the stapes and the incus and comprising fixing means for securing to at least one of said stapes and said incus and formed and arranged so that when activated in response to a signal derived from sound, said actuator displaces the stapes relative to the incus such as to provide amplification of said sound signal in order to generate vibration levels that can exceed those vibration levels which, in the absence of said actuator, would normally be experienced by the ossicular chain for a given applied sound level of the source.

The actuators of the present invention make use of the realisation that, due to the flexibility of the incudostapedial joint, it is possible to achieve sufficient displacement of the ossicular bones, in particular the stapes, for amplification of sound by mounting an actuator to bones of the ossicular chain alone. Prior art devices such as the TICA™ device, hereinbefore described, have generally required mounting of the actuator to the skull in order to provide a fixed base relative to which the ossicular bones are displaced when the actuator vibrates. The known electromagnetic devices such as the SoundTec™ system require an electromagnetic transmitter mounted separately from the ossicular chain, with the magnet located on the ossicular chain. In such arrangements the magnet moves the ossicular bone or bones to which it is attached relative to the coil mounted, for example, in the outer ear. In contradistinction, by virtue of being in contact with both the stapes and the incus, the actuators of the present invention are coupled to both of these bones and when operated are caused to vibrate, positively displacing the stapes and incus bones, relative to each other. Actuators of the present invention operate in such a manner as to tend to push or pull these bones apart and together with a force and displacement giving sufficient amplification to provide a useful supplement to the hearing of patients with moderate (41-70 dB) to severe (>70 dB) sensorineural hearing loss.

Further, in marked contradistinction to prior art devices, such as most of the embodiments disclosed in U.S. Pat. No. 6,629,922 to Puria et al, which require irremedial destruction of some part of an ossicular bone, with the attendant irreversible loss of any possibility of preserving residual hearing in the event that removal might become necessary, actuators according to the present invention require no such irreversible surgery.

Preferably, the actuator of the present invention comprises a piezoelectric component wherein the expansion or contraction of a piezoelectric element or elements in response to an electrical signal is used to cause displacement of the stapes relative to the incus. The actuator of the present invention may comprise a piezoelectric component having one or more piezoelectric elements.

Preferably, the expansion or contraction of the piezoelectric component is mechanically amplified to drive the displacement of the stapes relative to the incus.

In such an embodiment, an actuator comprises a piezoelectric component in the form of an element of piezoelectric material, or a plurality of elements of piezoelectric material forming a stack, or a plurality of stacks in the form of an array, and a mechanical amplifier component formed and assembled as a single frame component to amplify the expansion or contraction of said piezoelectric component when it is activated in response to an electrical signal. Preferably, the mechanical amplifiers of the present invention are flextensional amplifiers comprising a one-piece frame component constructed from resilient material, such as for example titanium and formed with integral first and second end portions disposed substantially at right angles to said flextensional amplifiers providing means for enclosing or otherwise containing first and second operating ends and end faces of the piezoelectric component.

Preferably, with the present invention, a single frame component of modified rectangular form has first and second end portions which are of a length somewhat greater than those of the dimensions of the first and second operating end faces of the piezoelectric component. The frame component has first and second preferably curved sides which are of substantially similar effective chordal length to the longitudinal dimension of the piezoelectric component (i.e. the distance between the operating end faces of the piezoelectric component) and function as flextensional amplifiers. It will be understood from the foregoing that first and second end portions of said frame component are disposed substantially at right angles to said first and second curved sides of said frame component constituting said first and second flextensional amplifiers.

Advantageously, the flextensional amplifiers of the first and second sides of the frame component are formed and arranged so as to be arcuate in shape with the curvature increasing or decreasing in response to the expansion or contraction of the piezoelectric component, the orientation of the piezoelectric component being the determinant of whether expansion or contraction causes increase or decrease in curvature of the flextensional amplifiers.

Desirably, the piezoelectric component and the frame component may be secured together with securing means which may be in the form of adhesive means such as a resin based adhesive or mechanical means such as small fold down tabs on the first and second end portions of the frame component or recesses in the integral first and second end portions of the frame component. Also advantageously, though not necessarily, the actuator may be provided with housing coating or covering means to isolate one or more of its parts from the local environment. Also advantageously, flextensional amplifiers of the present invention are provided with base support means for the fixed attachment of securing means which may comprise, for example, clips for securing the actuator to the stapes and incus, for example only, by crimping or by spring clip means.

By means of this inventive arrangement the actuator frame component of the present invention can provide two flextensional amplifier elements from only one unitary component. The flextensional amplifier elements respond to the small expansions and contractions of the piezoelectric component to which they are coupled by bending so as to generate actuator displacements of greater amplitude than would be the case with the piezoelectric component alone.

Flextensional amplifiers have been previously employed with piezoelectric elements for other applications. The present invention, when used for the primary application, makes use of particularly small piezoelectric components and frame components to provide actuators having only two main components of a size suitable for use in the middle ear, attached to the ossicular chain, without destruction of any part thereof. By way of non-limiting example, preferred embodiments do not exceed 2.5 mm in any dimension (measured without ossicular chain attachment means).

Preferably, the piezoelectric component of the present invention is in the form of a multilayer stack of layers of piezoelectric material or an array of stacks of layers of piezoelectric material. This can give the benefit of producing large driving forces and large displacements when the actuator is activated by an electrical signal.

Desirably the piezoelectric component has piezoelectric elements constructed of a piezoelectric material, such as Lead Zirconate Titanate (PZT), preferably in the form of a multi-layer stack or stacks of piezoelectric material.

The actuators of the present invention may comprise piezoelectric elements, stack or arrays which are very small and also operate at low levels of power consumption. They can be inserted into the middle ear via the ear canal and incised and folded back eardrum (tympanum), the simplest and most common approach in middle ear surgery. Desirably, very small actuators according to the present invention may be attached to the ossicular chain without the requirement to destroy or damage any part thereof during surgery, thereby ensuring that there is no loss of residual hearing in the event that removal of the implanted actuator might be indicated or required for any reason. This is in marked contradistinction to prior art devices. The sound information signal and power can be provided by direct wiring to the actuator, with the power source being a battery or other storage cell or storage device such as a capacitor for example.

Preferably the signal and power transmission system disclosed in the applicants' pending International patent application WO 03/063542 is used. This system utilises a light signal from a source mounted in the external ear canal to carry sound information to the actuator via a photoreceiver inside the middle ear that converts the light signal to an electrical input for the actuator, and in some cases, can provide power to the photoreceiver and other electronic components. The photoreceiver may be mounted directly on the actuator or may be placed elsewhere in the middle ear and connected to the actuator by suitable wiring.

Other means of powering the actuators of the invention, such as inductive coupling, can be envisaged. A totally implantable device, without the requirement for a battery or external power source, can be realised by operating the actuators of the invention with electrical signals derived from a piezoelectric sensor or sensors. The sensors produce electrical signals in response to sound vibrations and are located within the ear.

Fixing means is formed and arranged for mounting said actuator to at least one of the stapes or incus bones of a middle ear. A number of different fixing means are possible and some preferred embodiments are described later. Where the fixing means attaches the actuator to only one of the stapes or the incus the actuator is fixed in such a way that it contacts the other bone and so is coupled to both bones. When the actuator operates it displaces the stapes relative to the incus.

Preferably, the fixing means attaches the actuator to the stapes. More preferably the fixing means comprises crimpable, spring or other clip means having three tines, two of which fit closely to the stapes head and the other fits between the crus structures near the junction with the stapes head. Fixing means can be used either with an actuator attached to the stapes from an inferior (bottom) or from a superior (top) approach. Attachment to the incus by a second fixing means such as, for example, crimpable, spring or other clip means comprising two resilient tines provides appropriate contact therewith.

Where attachment is to the stapes by, for example, a superior approach the actuator can simply contact the incus by being positioned against it when attached to the stapes by crimpable, spring or other clip means but second fixing means, such as second crimpable, spring or other clip means, can also be used.

Alternatively, attachment to the stapes can be by, for example, a side approach using as fixing means, for example, crimpable clip means for attachment to the side of the stapes head and further crimpable clip means for attachment to the incus in order to provide good contact of the actuator with both bones.

A side approach may be preferred in surgical practice because of the limited available space surrounding the ossicles when the approach is made from other directions.

Preferably the fixing means attaches the actuator to both the incus and the stapes, by means of crimpable clip, spring or other clip means comprising clips of suitable design and configuration according to the direction of approach of attaching the actuator.

Preferred embodiments of the actuators of the present invention comprise, as the piezoelectric component, a multilayer stack or an array of stacks of piezoelectric elements. Such stacks are well known and can be constructed to operate in a contractive (d31) or expansive (d33) mode or a combination of both modes. The mode may be defined according to the orientation of the stack or stacks in relation to the mechanical amplifier. In the d31 mode, on application of a voltage, there is contraction of the stack of elements in the direction of the line between the two end portions of the frame component, while in the d33 mode, on application of a voltage, the stack expands in the direction of the line between the two end portions of the frame component.

A preferred embodiment of the actuator of the present invention comprises a piezoelectric component in which two d31 mode piezoelectric stacks are spaced apart by base support means in the form of a base support attached to adjacent ends of said stacks to form a generally longitudinal piezoelectric array. The piezoelectric array constituting the piezoelectric component is secured to a frame component comprising a flextensional amplifier of generally longitudinal form having a length greater than said piezoelectric array constructed from a resilient material, said frame component being provided at each end with integral first and second end portions each being disposed substantially at right angles to said flextensional amplifier to form a frame component of open design fixed by fixing means to the first and second operating end faces of the piezoelectric component, said flextensional amplifier having an arcuate form curving outward from the piezoelectric component. When the piezoelectric component is activated and contracts, the flextensional amplifier increases in curvature, moving in a direction generally away from the piezoelectric component. The base support is used to attach the actuator to fixing means for mounting the actuator to the selected ossicular bone.

In a further preferred embodiment, an actuator comprises a frame component provided with dual flextensional amplifiers each being of generally longitudinal form and provided with integral first and second end portions each being disposed substantially at right angles to said dual flextensional amplifiers and each of said integral first and second ends of said frame component being secured about the first and second operating ends of a longitudinal piezoelectric array constituting the piezoelectric component, said dual flextensional amplifiers being positioned in an opposed manner so that when said piezoelectric component is operated and contracts the bodies of said dual amplifiers move in a direction generally away from each other as they increase in curvature. This arrangement can give the benefit of a symmetrical loading of the piezoelectric component, avoiding significant tensile stresses in the array which could lead to breakage of a multilayer piezoelectric stack. A further benefit is that the amplification of the contraction movement of the piezoelectric component by the dual flextensional amplifiers is doubled by virtue of the movement of each of the amplifiers in opposite directions. Advantage may be taken of this doubled amplification if the dual flextensional amplifiers are located between the bones which are to be moved relative to one another, rather than attaching the actuator by means of a base support provided with suitable attachment means, to one bone and one flextensional amplifier also provided with a base support provided with suitable attachment means, to the other bone.

In an alternative, preferred embodiment, use is made of a d33 (expanding) piezoelectric stack or array to provide the piezoelectric component. In such an embodiment, the frame component has a single flextensional amplifier or dual flextensional amplifiers which can be configured differently.

A generally longitudinal piezoelectric component, which may comprise one d33 stack or an array of d33 stacks placed end to end, is assembled to a frame component having integral first and second end portions each being disposed substantially at right angles to said single or dual flextensional amplifiers and each of said integral first and second ends of said frame component being secured about the first and second operating ends of a longitudinal piezoelectric component.

In this case the single or dual flextensional amplifiers are arcuate in form, curving towards the piezoelectric component, with the integral first and second end portions acting as spacers to distance the single or dual flextensional amplifiers from the piezoelectric component. When the piezoelectric component is activated and expands the bodies of the single or dual flextensional amplifiers decrease in curvature and move away from the piezoelectric component: Where dual flextensional amplifiers are employed they are disposed substantially at right angles to said integral first and second end portions of said frame component in an opposed fashion so that when the piezoelectric component is activated they move in opposite directions, generally orthogonal to the longitudinal axis of the piezoelectric component. In this embodiment the base support may be positioned on the piezoelectric component or on a flextensional amplifier, the latter design affording double the amplification of the former.

In a further preferred embodiment of the actuator a piezoelectric component comprising a d33 (expansive) piezoelectric stack is used together with a frame component comprising two flextensional amplifiers substantially disposed at right angles to integral first and second end portions. Frame components are preferably made of titanium or titanium alloy.

The present invention provides an actuator for use in a middle ear implant, said actuator comprising a piezoelectric component and a frame component providing one or dual flextensional amplifiers formed and arranged for amplification of the displacement of the piezoelectric component when said piezoelectric component is activated in response to a signal derived from a sound vibration.

Generally the frame component may comprise a single piece of resilient material having single or dual flextensional amplifiers each being of generally longitudinal form and provided with integral first and second end portions each being disposed substantially at right angles to said single or dual flextensional amplifiers and each of said integral first and second ends of said frame component being secured about the first and second operating ends of a piezoelectric stack constituting the piezoelectric component. Said single or dual amplifiers may have a curved form. Preferably, when the piezoelectric component is activated and expands or contracts the relatively small displacement at the ends of said piezoelectric component causes a larger displacement, manifested as a change in curvature in the single or dual flextensional amplifiers. This displacement is preferably generally orthogonal to the longitudinal axis of the piezoelectric stack.

According to a further aspect of the present invention there is provided a method of forming an actuator for an implantable hearing aid for implantation into the human middle ear, the method comprising the steps: providing a substantially elongate piezoelectric component having first and second operating end faces, said end faces extending substantially at right angles to the longitudinal axis of the piezoelectric component; providing a frame component comprising at least one flextensional amplifier element, the flextensional amplifier element being integral with and connecting first and second frame end portions, the first and second frame end portions also extending substantially at right angles to longitudinal axis of the piezoelectric component when fitted thereto, whereby the first and second end portions are in contact with the piezoelectric component end faces, and assembling the piezoelectric component and the frame component.

Preferably, the assembled actuator is surgically implantable into the middle ear through the ear canal and via the incised and folded back tympanum.

In marked contradistinction to the device of Puria et al in U.S. Pat. No. 6,629,922, the flextensional amplifier structures of the frame component of the present invention are not fixedly attached to a first or second planar surface but are integral with first and second end portions providing securing means for securing said frame component to first and second ends, respectively, of a piezoelectric component. This has the effect of reducing the minimum total number of components from three to two and the amplifier elements to one (by virtue of being always integral with a frame component). The incorporation of integral first and second end portions in frame components of the present invention can markedly improve structural integrity of the actuator since there is no reliance on adhesives to maintain functionality of the actuator; this can be particularly important in the context of an implantable device. The potentially difficult mandatory step disclosed in U.S. Pat. No. 6,629,922 to Puria et al, namely assembly with adhesives, is also substantially eliminated in the present invention. Further, the required step of destruction of part of the ossicular chain disclosed in most embodiments in U.S. Pat. No. 6,629, 922 to Puria et al is obviated in all embodiments of the present invention.

Further preferred features and advantages of the present invention will appear from the following detailed description of some embodiments illustrated with reference to the accompanying drawings in which.

Figure 7A:
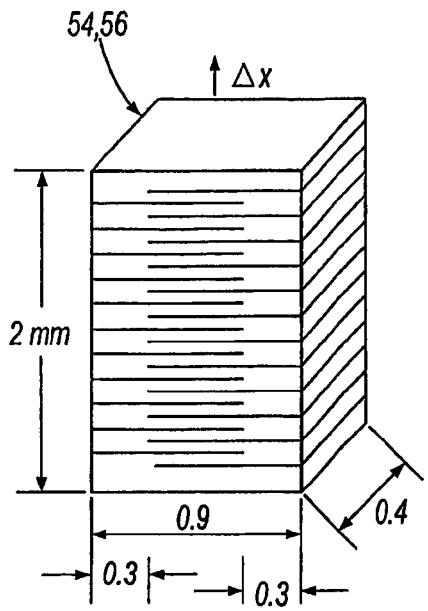
FIG. 7a shows a d33 piezoelectric stack used in actuators of the present invention.
Figure 7B:
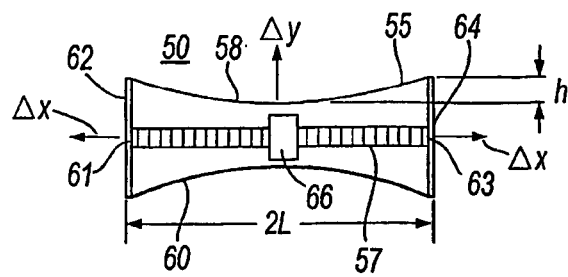
Figure 8A:
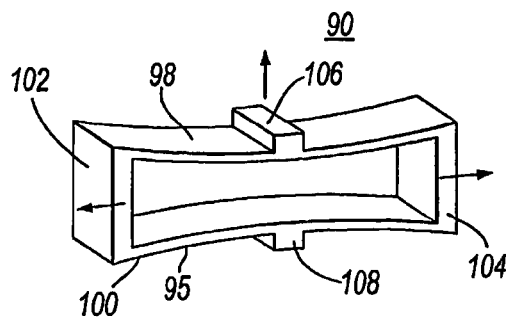
Figure 9A:
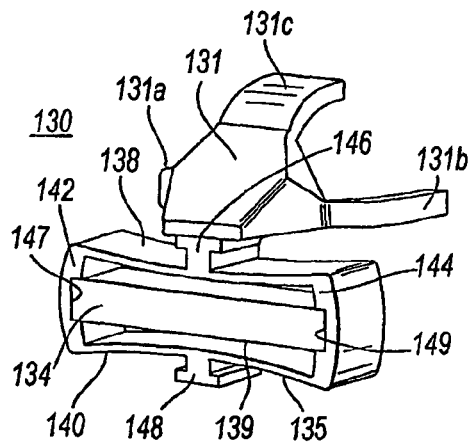
Figure 10:
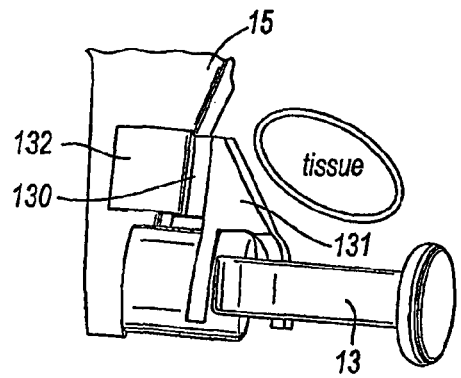
Figure 11A:
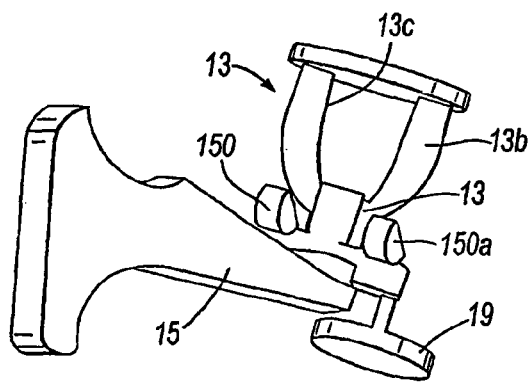
Figure 12A:
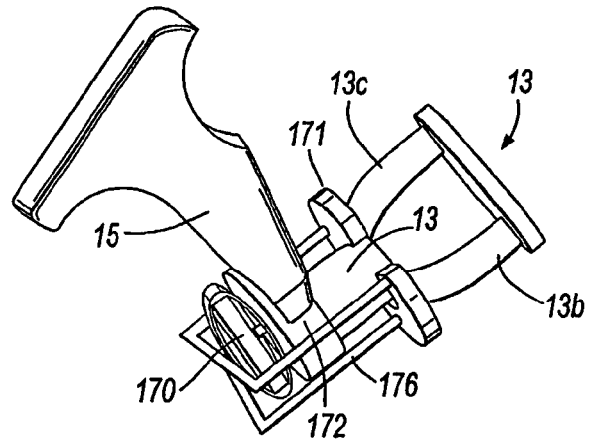
Figure 12B:
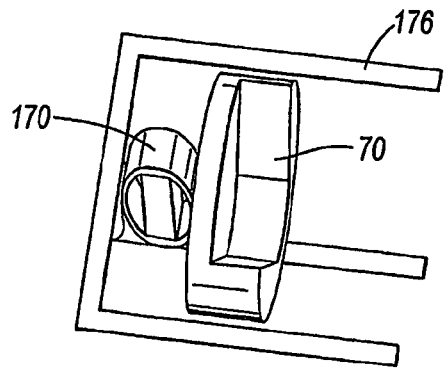
Figure 12C:
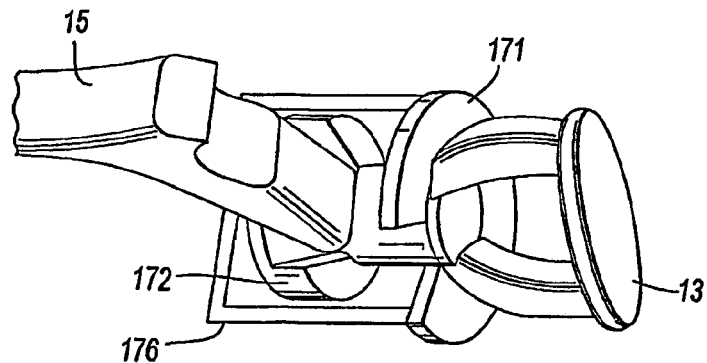
Figure 13A:
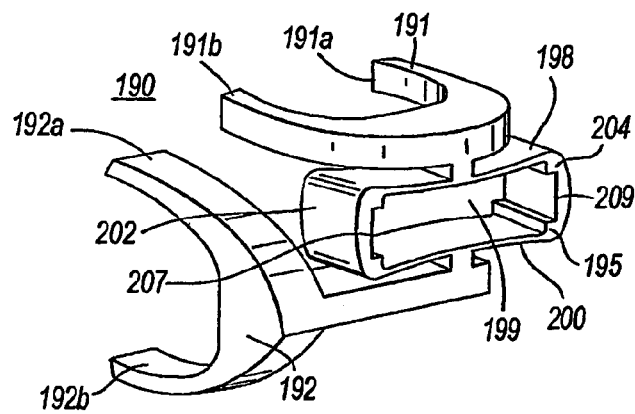
Figure 14:
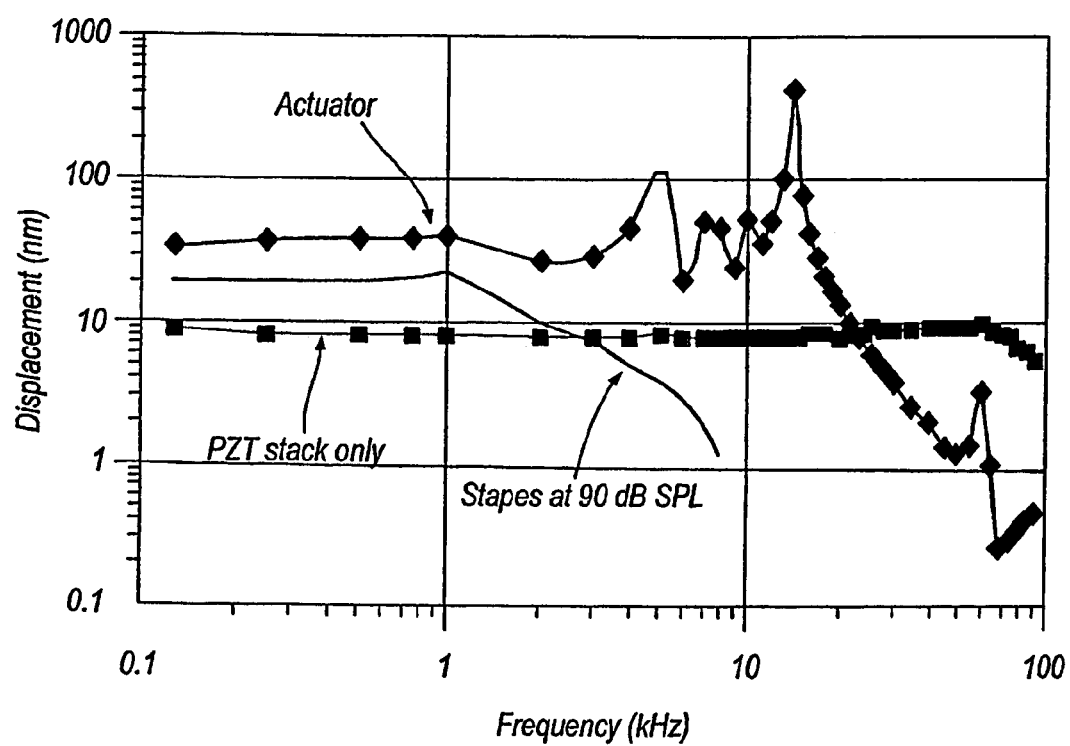

FIGS. 7b and c show diagrammatically two embodiments of actuators according to the present invention comprising a piezoelectric component utilising d33 stacks;

FIGS. 8a and b show two further embodiments of actuators of the present invention;

FIGS. 9a and b show two views of a preferred embodiment of an actuator of the present invention with attachment and mounting means for attachment to the ossicular chain by an inferior (bottom) approach;

FIG. 10 shows a further preferred embodiment with attachment and mounting means for attachment to the ossicular chain by a superior (top) approach;

FIGS. 11a, b and c show three views of an embodiment with two actuators according to the present invention with attachment and mounting means for attachment to the ossicular chain by a superior approach;

FIGS. 12a, b and c show an embodiment of a single actuator of the present invention having attachment and mounting means for attachment to the incus long process;

FIGS. 13a and b, show a preferred embodiment of an actuator of the present invention with attachment and mounting means for attachment to the ossicular chain by a side approach;

FIG. 14 shows graphically the amplification of the displacement of an actuator of the present invention utilising a PZT based piezoelectric stack and comprising flextensional amplifiers of the present invention.

1. D31 MULTI-LAYER BASED ACTUATORS

A small multi-layer based actuator 30 is briefly described here and shown in FIG. 4. For clarity the fixing means for attaching the actuator to the ossicular bones and the means for supplying the sound information signal and power are not shown.

Figure 1:
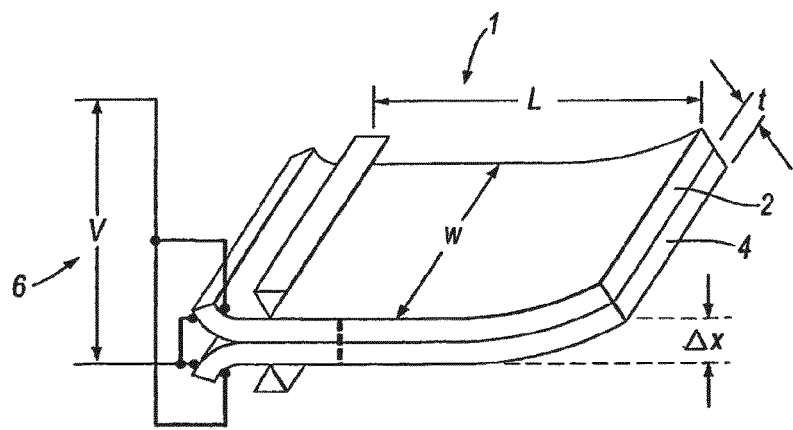
FIG. 1 is a schematic representation of a bimorph piezoelectric transducer of a prior art P-MEI™ partially implantable middle ear implant.
Figure 2:
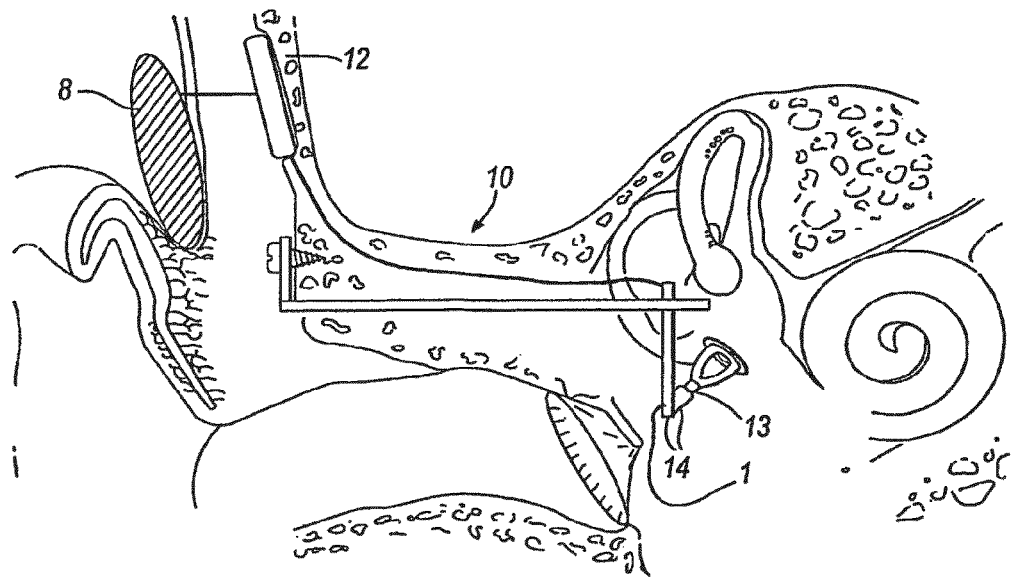
FIG. 2 is a drawing of a prior art P-MEI™.
Figure 3A:
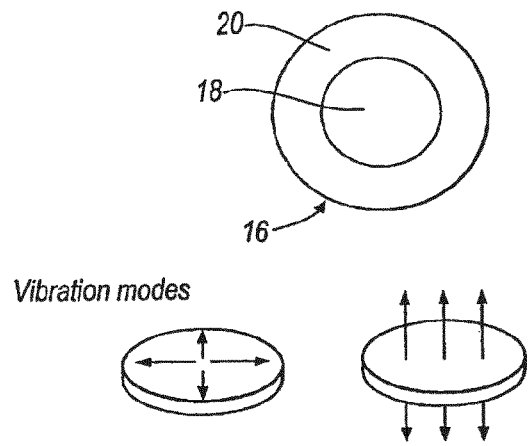
FIG. 3a is a schematic representation of a ceramic disc piezoelectric element used in the prior art TICA™ middle ear implant.
Figure 3B:
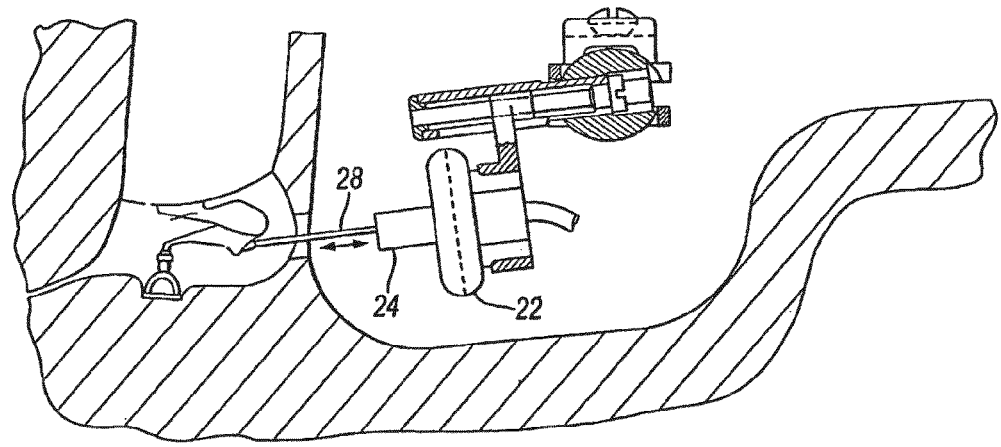
FIG. 3b is a drawing of the prior art TICA™ device located in an ear, coupling to the ossicular bones.
Figure 4A:
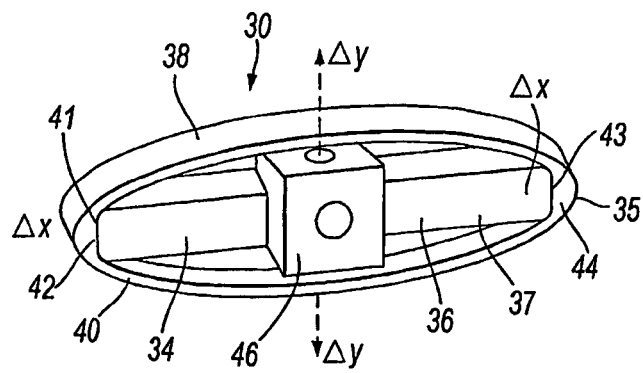
FIG. 4a shows an actuator of the present invention comprising a piezoelectric component having an array of two piezoelectric stacks in a d31 configuration and a frame component having dual flextensional amplifiers.

FIG. 4a illustrates an actuator 30 which amplifies displacement generated by a piezoelectric component 37 having two multi-layer piezoelectric stacks 34,36 forming a piezoelectric array. A frame component 35 comprises dual flextensional amplifiers 38,40 provided with integral first and second end portions 42,44 disposed substantially at right angles to 38,40, and positioned, respectively, at first and second end faces 41,43 of piezoelectric component 37.

Figure 5A:
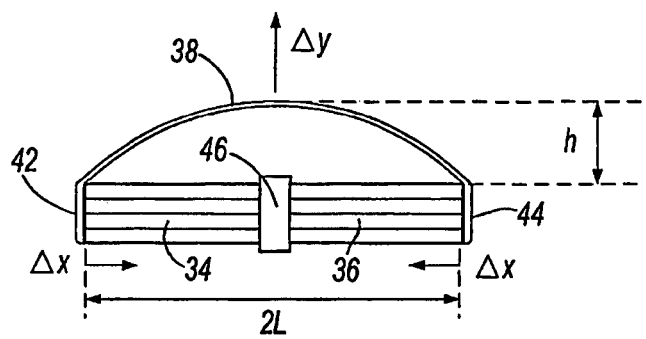
FIGS. 5a and 5b illustrate the mechanical amplification provided by a flextensional amplifier of the present invention.

Frame component 35, is preferably made of titanium (ASTM F67) Medical Grade—a material widely used by the hearing implant industry (referred to at http://www.kurzmed.co). The orientation of multilayer stacks 34,36 may be seen by brief reference to FIG. 5a, with a d31 contraction direction in the long axis of the piezoelectric component 37. When piezoelectric component 37 operates and contracts, dual flextensional amplifiers 38,40 function to mechanically amplify the small displacement Δx (stack length contraction) to a larger axial extension Δy, by bending with an increase in curvature. A base support 46, also made of titanium, is used to mount stacks 34, 36 and to support piezoelectric component 37. As indicated in FIG. 5a the reduced length of a piezoelectric stack in this arrangement has increased stiffness and a reduced tendency to buckle under compressive loading. Furthermore, the length of base support 46 may be chosen to reduce the total length of piezoelectric component 37 according to the magnitude of the displacement required for a given size of actuator. In addition, length of base support 46 may be chosen in order to vary the length of piezoelectric component 37 such that its electric capacitance and hence its current consumption may be controlled.

Figure 4B:
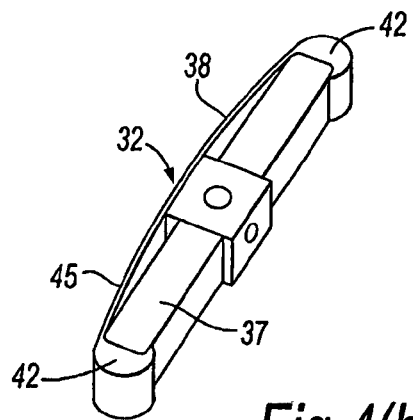
FIG. 4b shows an actuator of the present invention comprising a piezoelectric component having an array of two piezoelectric stacks and a frame component comprising a single flextensional amplifier.

FIG. 4b illustrates a variation 32 of actuator configuration 30, having a frame component 45, substantially similar to frame component 35 but being provided with only a single flextensional amplifier 38. This more compact design can also have the benefit of being easier to assemble to piezoelectric component 37 and mount to the ossicular chain.

The mechanical amplification by virtue of displacement is dependent on the structure of single curved flextensional amplifier 38, of frame component 45 in particular its stiffness, thickness and its curvature. With brief reference to FIGS. 5a and b, which represent the principle of operation for both a single flextensional amplifier contifugration and dual flextensional amplifiers, it may be seen that height h, together with length L, determine the amplification or gain according to G=(L)/h, Dogon et al. Therefore, the maximum displacement Δy and axial net force F3 at the spring middle point (apex) of 38 can be predicted by:

Δy=GΔx, and F3=F1/G where F1 is the lateral (contracting) force from one multi-layer stack.

For example, in the configurations given in FIGS. 4a and 4b, given L=1 mm and h=0.2 mm, this mechanical structure can produce amplification of displacement which is 5 times that of the displacement of piezoelectric component 37 alone.

Figure 6:
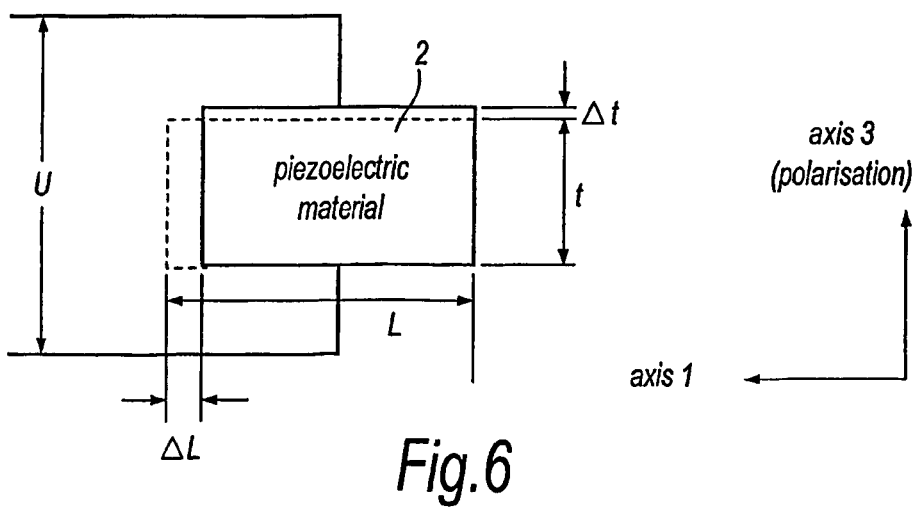
FIG. 6 illustrates the operation of a layer of piezoelectric material.

To generate the required contracting force and displacement, a d31 stack of multiple layers of piezoelectric material can be used and FIG. 6 illustrates how a single layer of piezoelectric material 2 functions. An electric voltage U is applied across the thickness direction (indicated in FIG. 6 as 'axis 3'), which causes mechanical expansion Δt in the thickness direction and contraction ΔL in the perpendicular direction (indicated in FIG. 6 as 'axis 1').

To give a design example, a single layer of piezoelectric material 2 with an active component of dimensions: L=1 mm, t=25 μm, W=0.6 mm, can generate displacement ΔL=12.8 nm (and Δt=0.65 nm) at 1 Volt using the formulas: Δt=d33U and ΔL=d31U(L/t) (where the coefficients d33 and d31 are from materials PZT-5H or Navy Type VI).

The device has a blocking force of about 12 mN (stiffness=0.93 N/μm) and capacitance of about 0.8 nF. A stack of multiple layers of piezoelectric material will provide an increased stiffness (providing higher driving capacity) but will also consume more electrical power due to the increased capacitance associated with having multiple layers. For example, a 6-layer stack will produce: ΔL=12.8 nm (with Δt=6*0.65=3.9 nm), blocking force F=72 mN and capacitance C=4.8 nF. Given a mechanical amplification of 5 (G=5), the flextensional amplifier of such an actuator, at 1 Volt applied voltage, will generate a displacement: Δy=5*12.8 nm=64 nm, and a driving force F3=72/5=14.4 mN and have a capacitance of only 4.8 nF. This is better than the reported TICA™ performance, yet it employs a much smaller structure.

2. D33 MULTI-LAYER BASED ACTUATORS

Figure 5B:
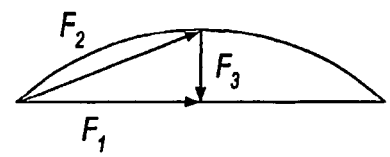

In FIG. 7b actuator 50 is shown diagrammatically and comprises a piezoelectric component 57 having an array of two, more compact and potentially stronger, d33 multi-layer stacks 54,56 (seen also with brief reference to FIG. 7a) and frame component 55. Base support 66 is disposed within array 57, between stacks 54,56. Since d33 stacks generate expansion, dual flextensional amplifiers 58,60 of frame component 55 each has an inwardly directed arcuate form curving towards piezoelectric component 57. Flextensional amplifiers 58,60 are integral with and disposed substantially at right angles to integral first and second end portions 62,64 of frame component 55. Integral first and second end portions 62,64 of frame component 55 are disposed in secure contact with first and second end faces 61,63, respectively, of piezoelectric component 57. The working principle and method of amplification estimation are similar to that hereinbefore described with reference to actuators 30,32 and FIG. 5.

Figure 7C:
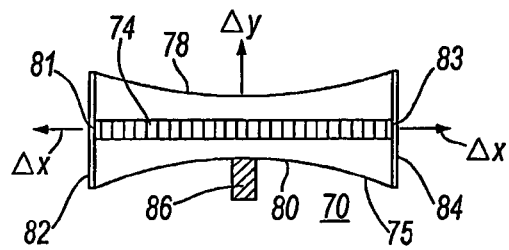

In FIG. 7c there is shown diagrammatically a preferred embodiment which takes advantage of the feature that an actuator based on a multi-layer d33 PZT stack or stacks can generate more force with less displacement. In this embodiment, actuator 70, comprises a piezoelectric component 74, having a single stack and frame component 75. Frame component 75 is provided with dual flextensional amplifiers 78,80 each of which has an inwardly directed arcuate form curving towards piezoelectric component 74. Frame component 75 also has integral first and second end portions 82,84 disposed substantially at right angles to flextensional amplifiers 78,80. Integral first and second end portions 82,84 of frame component 75 are disposed in secure contact with first and second end faces 81,83, respectively, of piezoelectric component 74. Advantageously, in this embodiment base support 86 is disposed at a location upon one of the flextensional amplifiers, for example 78, rather than within or disposed about piezoelectric component 57, as in the embodiment previously described with reference to FIG. 7b. In this latter arrangement, the relative motion between the points of fixation to two external bony components, such as the incus and stapes of the ossicular chain is, therefore, twice the magnitude of a mounting system where a base support (for example 66) is mounted on or in a piezoelectric component (for example 57).

As an example, a multi-layer stack having overall end dimensions of 0.9 mm×0.4 mm and a stack height of 2 mm, with active piezoelectric end dimensions of 0.4 mm×0.3 mm, a thickness of each piezoelectric layer of 30 μm, and 51 layers of piezoelectric material can generate a displacement Δx of around 15 nm at an applied voltage of 1 Volt (rms), with a blocking force of 89 mN and a capacitance of about 5 nF. Actuators according to the present invention have been designed and manufactured making use of a piezoelectric component comprising PZT stacks having properties substantially as immediately hereinbefore described.

Mechanical Amplifier Design

Figure 8B:
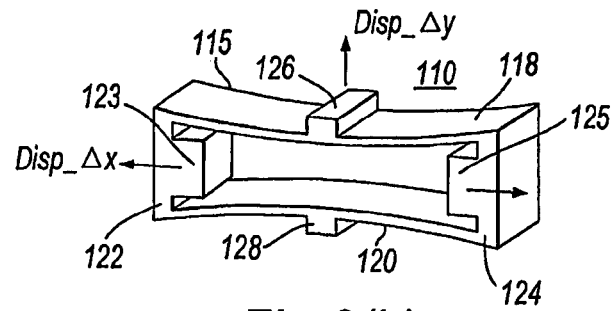

FIGS. 8a and 8b show two further embodiments of the present invention. Design calculations of their performance, utilising piezoelectric components substantially similar to the unit immediately hereinbefore described, have been made.

In the worked exemplary embodiment of FIG. 8a actuator 90 has a frame component 95 with an overall total length of 2.4 mm comprising dual flextensional amplifiers 98,100 and integral first and second end portions 102, 104 disposed substantially at right angles to flextensional amplifiers 98,100. Frame component 95 is formed so as to provide a press fit over and about the 2 mm height of the piezoelectric component comprising a stack which is omitted in FIG. 8a for clarity.

In the worked exemplary further embodiment of FIG. 8b actuator 110 is designed to increase the displacement by providing a frame component 115 having a longer length L, thereby providing longer dual flextensional amplifiers 118, 120. This is achieved by introducing integral first and second structural extensions 123,125 to each of integral first and second end portions 122,124, respectively, by means of which total length may be increased up to but not substantially more than 3 mm. Wall thickness of dual flextensional amplifiers 118,120 is preferably about 0.05 mm. The same piezoelectric component with a height of 2 mm was used in this embodiment as in that of the embodiment of FIG. 8a and is omitted in FIG. 8b for clarity.

Using computer modelling and design tools (ProMechanica™ FEA analysis and simulation), the initial characteristics with these embodiments are, for an applied voltage of 1 Volt (rms): a stack (piezoelectric component) displacement 15 nm with actuator 90 of FIG. 8a was amplified seven-fold by dual flextensional amplifiers 98,100 of frame component 95 and a displacement of 15 nm from the same stack (piezoelectric component) employed in this instance with actuator 110 of FIG. 8b was amplified eight-fold by dual flextensional amplifiers 118,120 of frame component 115, providing an output displacement in excess of 100 nm.

With the embodiment of FIG. 8b the driving force (reaction) is around 10 mN, with resonant frequency around 10 kHz. The total mass of the assembled actuators is less than 9 mg, and the buckling force is 1550 times larger that the PZT generated force of 88 mN. The actuators 90,110 of these embodiments also have a highly linear amplification response.

Mounting/Attachment to the Ossicular Chain Via Inferior (Bottom) Approach

FIG. 9a shows, in schematic form, a first view of a preferred embodiment of an actuator 130 of the present invention having a frame component 135 comprising two flextensional amplifiers 138,140 and two integral first and second end portions 142, 144. Each of end portions 142, 144 is disposed substantially at right angles to flextensional amplifiers 138, 140, and is thickened to provide the structural equivalents of extensions 123,125 of end portions 122,124 of frame component 115 of the embodiment of FIG. 8b. Integral first and second end portions 142, 144 are also provided with a first and second recess 147,149, respectively, which accommodate a piezoelectric component 134 comprising a d33 stack as a press fit within cavity 139 of frame component 135. Dual flextensional amplifiers 138,140 are each provided with a base support 146,148, respectively. The overall length of frame component 135 is just under 2.5 mm and the general wall thickness of dual flextensional amplifiers 138,140 is about 0.05 mm. Frame components according to the present invention may be made by the well known processes of electro-discharge machining or laser cutting. First base support 146 is fixedly attached to a stapes attachment means in the form of a stapes clip 131 having the form substantially of a crimpable mounting fork with three tines 131a, 131b, 131c, comprising attachment and mounting means for actuator 130 to the stapes bone of the human ossicular chain.

Figure 9B:
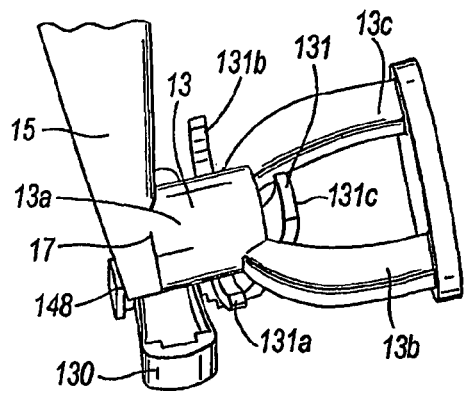

FIG. 9b illustrates actuator 130 mounted to the ossicular chain by stapes clip 131, with tines 131a,131b that can be crimped to the stapes head 13a and tine 131c held between the crus 13b,13c. Piezoelectric component 134 is omitted for clarity. Desirably an incus attachment means in the form of an incus clip (not shown) may be provided fixedly attached to base support 148, for attachment between second base support 148 and the incus 15, providing the necessary contact for operation of actuator 130. Connection means to the power/signal source is omitted for clarity. In use, the stapes 13, is moved relative to the incus 15, by the operation of actuator 130 making use of the flexibility of the incudostapedial joint 17. Stapes clip 131 may preferably be made in titanium or titanium alloy or from shape memory alloys making use of either the superelastic property or the shape memory property.

With a total mass of less than 10 mg, the mass loading on the ossicular chain by the preferred embodiments of the present invention is small and compares very favourably with prior art devices. For instance, Gan et al., *Mass Loading on*

*the Ossicles and Middle Ear Function*, found that a 22.5 mg SoundTec™ implant decreased stapes displacement by only 2.6 dB across the frequency range of 1 kHz to 8 kHz.

Mounting/Attachment to the Ossicular Chain Via Superior (Top) Approach

FIG. 10 shows, in schematic form, a detail of a further preferred embodiment in which actuator 130 is attached to the ossicular chain by means of a stapes clip 131 and an incus clip 132, as immediately hereinbefore described with reference to FIGS. 9a and 9b. Actuator 130 is mounted to the stapes 13, with stapes clip 131 and is also attached to the incus 15 by an incus clip 132. Stapes clip 131 and incus clip 132 may preferably be made in titanium or titanium alloy or from shape memory alloy making use of either the superelastic property or the shape memory property. Alternatively incus clip 132 is not used and actuator 130 is positioned in coupling contact with the incus 15, optionally with the provision of a plate (not shown) attached to second base support 148.

FIGS. 11a, b and c illustrate three views of an embodiment having two actuators 150,150a according to the present invention. In this embodiment actuators 150,150a are attached to the stapes 13. Actuators 150,150a are configured in parallel and supported by a common titanium base support 166. Common titanium base support 166 is effectively clamped to the stapes head 13a for example by suitable clip attachment means such as stapes clip 151 and is supported by the incus 15. Stapes clip 151 may preferably be made in titanium or titanium alloy or from shape memory alloy, making use of either the superelastic property or the shape memory property. By these means actuators 150,150a are tightly coupled to both crus 13b,13c of the stapes 13 superstructure, thereby ensuring good vibration energy transmission. A photodetector or other telemetry system receiver 19 can be integrated with the device in order to provide means for remote powering for actuators 150,150a and for receiving the sound information signal.

This design has the benefit that it symmetrically excites both crus of stapes superstructure along the line of action of natural motion of the stapes. The provision of two actuators 150,150a can also provide increased power in comparison to designs having a single actuator.

Mounting/Attachment to the Ossicular Chain at the Incus Long Process

Figure 11B:
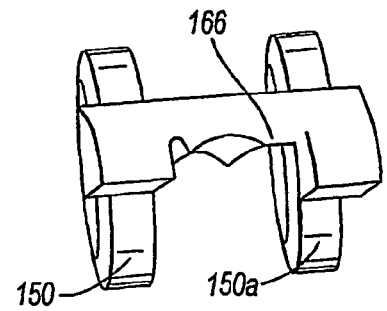
Figure 11C:
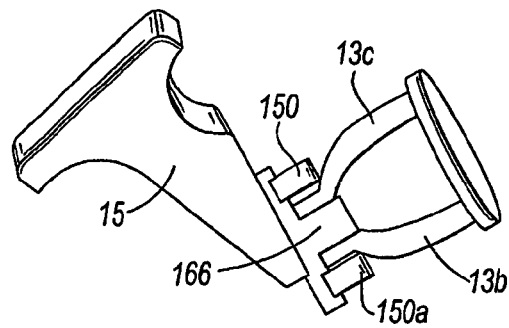

FIGS. 12a, b and c illustrate, schematically, details of an embodiment in which a single actuator 170 is mounted behind the incus 15. Actuator 170 is fixed to the incus 15 by a clip 172. Coupling to the crus 13b,13c is achieved by means of coupler 171, disposed about the stapes head 13a and biased towards crus 13b,13c by rods 176. As with the embodiment shown in FIG. 11, this arrangement provides vibration along the line of action of motion of the stapes.

Incus clip 172, coupler 171 and rods 176 may preferably be made in titanium or titanium alloy; incus clip 172 may also be made from shape memory alloy, making use of either the superelastic property or the shape memory property.

Mounting/Attachment to the Ossicular Via a Side Approach

Figure 13B:
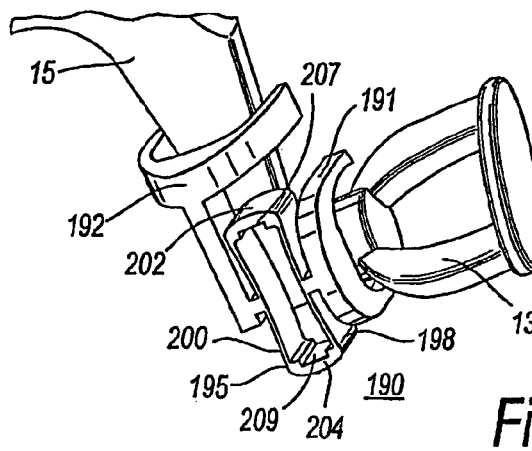

FIGS. 13a and 13b show two schematic views, not to scale, of a preferred embodiment in which actuator 190 has a frame component 195 which is substantially similar to frame component 135, of actuator 130, hereinbefore described in detail with reference to FIGS. 9a and 9b. Actuator 190 also has a piezoelectric component substantially similar to piezoelectric component 134 (comprising a single d33 stack) of actuator 130, also hereinbefore described in detail with reference to FIGS. 9a and 9b, and which is securely received as a firm press fit within recesses 207,209 of cavity 199 of frame component 195. The piezoelectric component is omitted in both FIGS. 13a and 13b for clarity.

FIG. 13a shows attachment means for attaching actuator 190 to the stapes 13 and the incus 15, from the side, in the form of a stapes clip 191 and an incus clip 192. Due to the limited space surrounding the ossicles a side approach may be preferred. Frame component 195 is provided with a first base support 206 fixedly attached to a stapes clip 191 which has the form substantially of a crimpable mounting fork with two tines 191a,191b comprising attachment and mounting means for actuator 190 to the stapes 13. Frame component 195 is also provided with a second base support 208 fixedly attached to an incus clip 192 also having the form substantially of a crimpable mounting fork with two tines 192a,192b comprising attachment and mounting means for actuator 190 to the incus 15. Frame component 195 incorporates flextensional amplifiers 198,200 and integral first and second end portions 202,204 disposed substantially at right angles to 198,200, which are adapted by the provision of recesses 207,209, respectively, to provide receival and securing means for the piezoelectric component within cavity 199, of frame component 195.

FIG. 13b illustrates actuator 190 mounted to the ossicular chain by stapes clip 191, with tines 191a,191b crimped to the stapes head 13a. and incus clip 192 with tines 192a,192b crimped to the incus 15.

Stapes clip 191 and incus clip 192 may preferably be made in titanium or titanium alloy or from shape memory alloy, making use of either the superelastic property or the shape memory property.

An advantage in this, preferred, embodiment is that actuator 190 is securely assembled by a simple firm press fit of the first and second operating ends of the piezoelectric component into recesses 207,209 of cavity 199 of frame component 195. Once assembled, the piezoelectric component will always tend to move so as to preserve the assembly even though it is not bonded to frame component 195. Actuator 190 is thus an inherently stable assembly.

It is to be understood that stapes clips and incus clips may be of an alternate design comprising spring means in the form of spring clips preferably made in titanium or titanium alloy or from shape memory alloy, making use of either the superelastic property or the shape memory property.

Alternate means for securing a piezoelectric component within a frame component are not illustrated because they are not normally considered necessary in a d33 embodiment, but may be used to enhance stability of the components. However, in d31 mode embodiments such alternate securing means may include the use of suitable adhesives or the provision of fold down tabs, formed at manufacture, and disposed at suitable positions about the periphery of integral first and second end portions. Further attachment means, such as making use of flexible wires can be envisaged.

It is to be understood that when d33 piezoelectric components are used, as hereinbefore described, advantage is taken of the feature that the piezoelectric component expands when activated by an electric signal, causing it to press against the frame component during displacement and obviating the need to use supplementary securing means (beyond the disclosed provision of recesses in the novel frame component). This critical enhancement to the structural integrity of actuators for use in challenging environments, such as for implantation into the human body, is not possible with prior art actuators, such as those disclosed in U.S. Pat. No. 6,629,922 to Puria et al which rely on a shear-loaded adhesively secured assembly.

It is to be understood that the sound information signal and power for actuators of the present invention can be provided by direct wiring to the actuator with the power source being a battery or other storage cell or storage device such as a capacitor for example.

Advantageously, actuators according to the present invention may be provided with housing, coating or covering means to isolate one or more of its parts from the local environment. Housing means may be in the form of a suitable metals or plastics enclosure or membrane.

Actuator Test Results

FIG. 14 shows graphically experimental test results for an actuator of the present invention, with the dimensions and other properties referred to in the calculations hereinbefore disclosed. The piezoelectric stack itself gives about 8.1 nm displacement at an applied voltage of 1 Volt peak to peak. The actuator output displacement with mounting means disposed substantially as shown in FIG. 10 (but without an incus clip) is 38.5 nm at up to 1 kHz (Gain=4.75), with mean displacement up to 46.3 nm up to 8 kHz (Gain=5.7) and 62.8 nm up to 20 kHz (Gain=7.75) due to resonance. Normal stapes displacement at 90 dB SPL sound stimulation at the eardrum is about 20 nm up to 1 kHz, decreasing with higher frequencies.

Although the present invention has been described with particular reference to a limited number of preferred embodiments, it will be apparent to those skilled in the art that variations and modifications of the present invention may be effected without departing from the scope of the present invention as defined in the following claims.

The invention claimed is:

1. An actuator for a hearing aid for implantation into a human middle ear and for moving a stapes relative to an incus of an incudostapedial joint, the actuator comprising:
   an elongate piezoelectric component having first and second operating end faces, said end faces extending substantially at right angles to the longitudinal axis of the piezoelectric component;
   a frame component comprising one or more flextensional amplifier element for amplifying displacements of the piezoelectric component, each of the one or more flextensional amplifier element being integral with and connecting first and second frame end portions, the first and second frame end portions also extending substantially at right angles to the longitudinal axis of the piezoelectric component when fitted thereto, whereby the first and second frame end portions receive the piezoelectric component first and second operating end faces,
   wherein at least one of the one or more flextensional amplifier elements is provided with base support means attached to a first clip means configured to secure the actuator to one of the incus and the stapes; and
   a second clip means configured to couple the actuator to the other of the incus and the stapes,
   wherein the first clip means and the second clip means being configured such that the actuator is mountable to extend from the incus to the stapes without separation of the incus and stapes at the incudostapedial joint.

2. An actuator according to claim 1, wherein said piezoelectric component operates in d33 expanding mode.

3. An actuator according to claim 1, wherein said piezoelectric component operates in d31 contracting mode.

4. An actuator according to claim 1, wherein said frame component comprises two flextensional amplifier elements.

5. An actuator according claim 1, wherein said one or more flextensional amplifier elements have a arcuate form with curvature directed towards said piezoelectric component.

6. An actuator according to claim 1, wherein said one or more flextensional amplifier elements have a arcuate form with curvature directed away from said piezoelectric component.

7. An actuator according to any one of claim 1, wherein said piezoelectric component comprises one or more stacks of piezoelectric elements.

8. An actuator according to claim 1, wherein said piezoelectric component comprises an array of stacks of said piezoelectric elements and said stacks are disposed apart from one from another by the base support.

9. An actuator according to claim 1, wherein a duality of said base supports is provided, fixedly mounted respectively upon each of a duality of said flextensional amplifiers of said frame component.

10. An actuator according to claim 1, wherein said integral first and second end portions of said frame component have substantially the same thickness as a wall thickness of said flextensional amplifiers.

11. The actuator according to claim 1, wherein said integral first and second end portions of said frame component have greater thickness than a wall thickness of said flextensional amplifiers.

12. An actuator according to claim 1, wherein said integral first and second end portions of said frame component each is provided with a recess so sized and shaped as to constitute receival and securing means for said first and second operating ends of said piezoelectric components.

13. An actuator according to claim 1, wherein said integral first and second end portions of said frame component is each provided with fold down tabs, whereby the folding down of said fold down tabs constitutes means for creating receival and securing means for said first and second operating ends of said piezoelectric components.

14. An actuator according to claim 1, wherein said integral first and second end portions of said frame component each are secured to said first and second operating ends of said piezoelectric component by securing means in the form of adhesive means.

15. An actuator according to claim 1, wherein said actuator is powered by a photodetector device.

16. An actuator according to claim 1, wherein said actuator is powered by a telemetry device.

17. An actuator according to claim 1, wherein said actuator is powered by a battery.

18. An actuator according to claim 1, wherein said actuator is powered by a induction coil.

19. An actuator according to claim 1, wherein said actuator is powered by a storage device such as a capacitor.

20. An actuator according to claim 1, wherein at least one of said first and second clip means is in the form of crimpable clip.

21. An actuator according to claim 1, wherein at least one of said first and second clip means is in the form of spring clip.

22. An actuator according claim 1, wherein said first and second clip means are adapted to be disposed about the incudostapedial joint.

23. An actuator according to claim 1, wherein at least one of said first and second clip means is made from titanium or titanium alloy.

24. An actuator according to claim 1, wherein at least one of said first and second clip means is made from a shape memory alloy making use of the shape memory property.

25. An actuator according to claim 1, wherein at least one of said first and second clip means is made from a shape memory alloy making use of the superelastic property thereof.

26. An actuator according to claim 1, wherein said actuator is provided with housing means to isolate one or more of its components from the local environment.

27. An actuator according to claim 26, wherein said housing means is in the form of an enclosure or membrane.

28. An actuator according to claim 26, wherein said housing means is made of plastics.

29. An actuator according to claim 1, wherein said actuator is provided with coating means to isolate one or more of its components from the local environment.

30. An actuator according to claim 1, wherein said actuator is provided with covering means to isolate one or more of its components from the local environment.

31. An actuator according to claim 1, wherein when the actuator is coupled to the ossicular chain of a user, the stapes is movable relative to the incus by the operation of said actuator making use of the flexibility of the incudostapedial joint.

32. A method for surgically implanting an actuator according to claim 1, the method comprising inserting the actuator into the middle ear via the ear canal and incising and folding back the eardrum.

33. A method of forming an actuator for a hearing aid for implantation into a human middle ear and for moving the stapes relative to the incus, the method comprising:
   providing an elongate piezoelectric component having first and second operating end faces, said end faces extending substantially at right angles to the longitudinal axis of the piezoelectric component;
   providing a frame component comprising at least one flextensional amplifier element, the flextensional amplifier element being integral with and connecting first and second frame end portions, the first and second frame end portions also extending substantially at right angles to longitudinal axis of the piezoelectric component when fitted thereto, whereby the first and second end portions are in contact with the piezoelectric component first and second operating end faces;
   assembling the piezoelectric component and the frame component;
   whereby the first and second frame end portions receive the piezoelectric component first and second operating end face;
   providing a base support means to at least one of the one or more flextensional amplifier elements;
   providing a clip means to the base support, the clip means being configured to couple the actuator to one of the incus and the stapes; and
   providing another clip means configured to couple the actuator to the other of the incus and the stapes;
   the clip means being configured such that the actuator is mountable to extend from the incus to the stapes without separation of the incus and stapes at the incudostapedial joint.

34. A method according to claim 33, wherein the assembled actuator is surgically implantable into the middle ear through the ear canal and by incising and folding back the tympanum.

* * * * *